US009545193B2

(12) United States Patent
Kaneko et al.

(10) Patent No.: US 9,545,193 B2
(45) Date of Patent: Jan. 17, 2017

(54) ENDOSCOPE APPARATUS (71) Applicant: OLYMPUS CORPORATION, Tokyo (JP)

(72) Inventors: Kazuma Kaneko, Hachioji (JP); Tomoki Iwasaki, Fuchu (JP); Susumu Hashimoto, Hachioji (JP); Yuji Kutsuma, Kokubunji (JP); Susumu Kawata, Hachioji (JP); Soichiro Koshika, Mitaka (JP); Tadao Eto, Musashino (JP); Takahiro Tanabe, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/804,554

(22) Filed: Jul. 21, 2015

(65) Prior Publication Data

US 2015/0320301 A1 Nov. 12, 2015

Related U.S. Application Data (63) Continuation of application No. PCT/JP2014/051368, filed on Jan. 23, 2014.

(30) Foreign Application Priority Data

Mar. 25, 2013 (JP) ................................. 2013-062433

(51) Int. Cl.
*A61B 1/06* (2006.01)
*G06K 9/00* (2006.01)
(Continued)

(52) U.S. Cl.
CPC ......... *A61B 1/0646* (2013.01); *A61B 1/00009* (2013.01); *A61B 1/05* (2013.01);
(Continued)

(58) Field of Classification Search
CPC ..... A61B 1/00186; A61B 1/043; A61B 1/045; A61B 1/0638; A61B 5/0075; A61B 1/00009; G06T 2207/10068; G06T 2007/10152; Y10S 600/931
See application file for complete search history.

(56) References Cited

U.S. PATENT DOCUMENTS

2011/0069199 A1   3/2011   Yamazaki
2012/0127292 A1   5/2012   Yamazaki

FOREIGN PATENT DOCUMENTS

EP        2347692 A1    7/2011
JP   2010-279454 A   12/2010
(Continued)

OTHER PUBLICATIONS

International Search Report dated Apr. 28, 2014 issued in PCT/JP2014/051368.

(Continued)

*Primary Examiner* — Thomas J Sweet
*Assistant Examiner* — Alexandra Newton
(74) *Attorney, Agent, or Firm* — Scully, Scott, Murphy & Presser, P.C.

(57) ABSTRACT

An endoscope apparatus has an illuminating unit that performs illumination with a first light once and performs illumination with a second light a plurality of times within a predetermined time period, an image pickup unit that outputs a first image pickup signal based on the illumination with the first light and a second image pickup signal based on the illumination with the second light, a clipping processing unit that clips the first and the second image pickup signals, a brightness calculating unit that calculates a first brightness, a composite ratio calculating unit that calculates a composite ratio according to a brightness target value and the first brightness, a composite processing unit that combines the first and the second image pickup signals accord- (Continued)

ing to the composite ratio, and a setting unit that sets a clip level according to the composite ratio.

8 Claims, 4 Drawing Sheets

(51) Int. Cl.
*A61B 1/05* (2006.01)
*A61B 1/07* (2006.01)
*A61B 1/00* (2006.01)
*G06T 5/50* (2006.01)

(52) U.S. Cl.
CPC .............. *A61B 1/0638* (2013.01); *A61B 1/07* (2013.01); *G06T 5/50* (2013.01); *G06T 2207/10024* (2013.01); *G06T 2207/10068* (2013.01); *G06T 2207/10152* (2013.01); *G06T 2207/20221* (2013.01); *G06T 2207/30004* (2013.01)

(56) References Cited

FOREIGN PATENT DOCUMENTS

| | | |
|---|---|---|
| JP | 4728450 B2 | 7/2011 |
| WO | WO 2010/131620 A1 | 11/2010 |
| WO | WO 2013/031701 A1 | 3/2013 |

OTHER PUBLICATIONS

Japanese Office Action dated Jan. 6, 2015 issued in JP 2014-532177.
Extended Supplementary European Search Report dated Aug. 9, 2016 received in European Application No. 14 77 4577.

ENDOSCOPE APPARATUS

CROSS REFERENCE TO RELATED APPLICATION

This application is a continuation application of PCT/JP2014/051368 filed on Jan. 23, 2014 and claims benefit of Japanese Application No. 2013-062433 filed in Japan on Mar. 25, 2013, the entire contents of which are incorporated herein by this reference.

BACKGROUND OF THE INVENTION

1. Field of the Invention

The present invention relates to an endoscope apparatus suitable for use in narrow band light observation.

2. Description of the Related Art

Because a medical endoscope is directed to observe inside of a living body, a light source apparatus for illuminating the inside of the body is required. An illumination light generated by the light source apparatus is radiated on an observation target tissue from a distal end portion of an image pickup unit through a light guide inserted through an insertion portion of the endoscope.

As observation using the endoscope, normal light observation which uses visible light such as white light has been widely performed. With a frame-sequential type endoscope apparatus, illumination lights of three colors of R, G and B are sequentially radiated on a tissue inside of a body cavity by allowing a light source of white light to pass through a rotating filter. Then, reflected light images corresponding to the illumination lights of three colors of R, G and B are acquired in time division to generate a color image from each reflected light image for performing normal light observation.

Further, conventionally, various kinds of special light observation which utilize wavelength characteristics of an illumination light have been also performed. For example, International Publication No. 2010/131620 discloses a frame-sequential type image pickup apparatus for performing narrow band light observation as special light observation. In the narrow band light observation, in order to observe a blood vessel at high contrast, by sequentially radiating a blue narrow band light and a green narrow band light on a living tissue while focusing attention on utilization of a light having characteristics of being strongly absorbed to the blood vessel and being strongly reflected and scattered in a mucous membrane surface layer, contrast between capillaries of the mucous membrane surface layer and a wide blood vessel in a deep portion is highlighted.

The invention disclosed in International Publication No. 2010/131620 is configured so that a green narrow band light G and two blue narrow band lights B1 and B2 can be sequentially radiated. Further, in the image pickup apparatus of International Publication No. 2010/131620, narrow band light observation is performed using a narrow band light observation image, created from reflected light images (narrow band images) corresponding to the narrow band lights G, B1 and B2. Still further, in the invention disclosed in International Publication No. 2010/1316120, an addition amount to be used in addition of an image obtained when the narrow band light B1 is radiated and an image obtained when the narrow band light B2 is radiated is determined based on average brightness of the image.

SUMMARY OF THE INVENTION

An endoscope apparatus according to one aspect of the present invention includes: an illuminating unit that performs illumination with an illumination light of a first band once and performs illumination with an illumination light of a second band N times (where N is an integer of N≥2), within a predetermined time period; an image pickup unit that picks up an image of an object illuminated by the illuminating unit and outputs a first image pickup signal based on the illumination with the illumination light of the first band and a second image pickup signal based on the illumination of the illumination light of the second band; a clipping processing unit that performs processing of limiting an upper limit value of a luminance value in the first image pickup signal and the second image pickup signal according to a clip level; a brightness calculating unit that calculates a first brightness on the basis of the first image pickup signal and the second image pickup signal based on illumination of K times (where K is an integer of 1≤K<N); a composite ratio calculating unit that calculates a composite ratio according to a difference value between a brightness target value and the first brightness; a composite processing unit that combines the first image pickup signal based on the illumination with the illumination light of the first band and the second image pickup signal based on the illumination of K times with the illumination light of the second band, the first and second image pickup signals generating the first brightness, with the first image pickup signal and the second image pickup signal based on illumination of N-K times with the illumination light of the second band, the first and second image pickup signals generating the second brightness; and a setting unit that sets the clip level according to whether or not the first and second image pickup signals which generate the first brightness are combined with the first and second image pickup signals which generate the second brightness by the composite processing unit, wherein the composite processing unit, after multiplying the first and the second image pickup signals which generate the second brightness by the composite ratio calculated by the composite ratio calculating unit, combines the multiplication-resultant first and second image pickup signals which generate the second brightness with the first and the second image pickup signals which generate the first brightness, and the setting unit sets the clip level according to the composite ratio calculated by the composite ratio calculating unit.

DETAILED DESCRIPTION OF THE PREFERRED EMBODIMENTS

Embodiments of the present invention will be described below with reference to the drawings.

Figure 1:
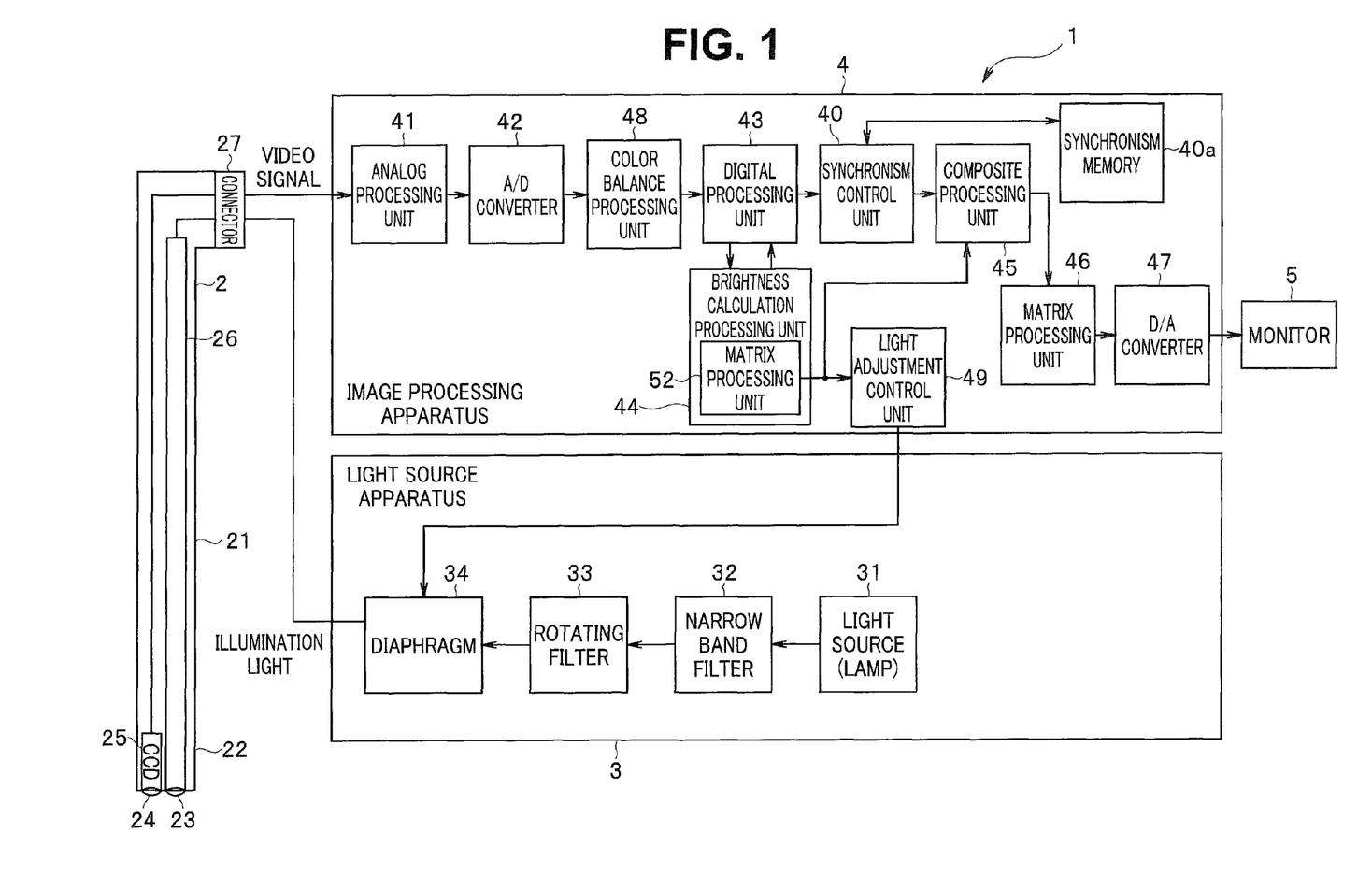
FIG. 1 is a block diagram illustrating one example of a configuration of an endoscope apparatus according to embodiments of the present invention.

FIG. 1 to FIG. 5 relate to the embodiments of the present invention. FIG. 1 is a block diagram illustrating a configuration of an endoscope apparatus according to the embodiments of the present invention.

As illustrated in FIG. 1, an endoscope apparatus 1 includes an endoscope 2 for observing inside of a living body which is a subject, a light source apparatus 3 which radiates a narrow band illumination light for observing the inside of the living body, and an image processing apparatus 4 which performs signal processing on an image pickup signal picked up under the narrow band illumination light. A narrow band image generated by the image processing apparatus 4 is supplied to a monitor 5. A normal color monitor can be employed as the monitor 5. That is, the monitor 5 includes an RGB input terminal (not illustrated), to which signals of an R image, a G image and a B image are supplied, so that color display is performed.

The endoscope 2 has a flexible insertion portion 21 having an outer diameter small enough to be inserted into a body cavity, and a light guide fiber 26 configured with a quartz fiber, or the like, for guiding an illumination light from the light source apparatus 3, is inserted into the insertion portion 21. One end of the light guide fiber 26 is connected to a connector 27 which is connected to the light source apparatus 3 so as to be able to be freely attached and removed. The other end of the light guide fiber 26 is disposed near an illumination lens 23 provided at a distal end portion 22 of a distal end of the insertion portion 21. Note that the connector 27 is connected to the light source apparatus 3 and is also connected to an image processing apparatus 4 which will be described later.

The illumination light from the light source apparatus 3 is guided to the distal end portion 22 of the insertion portion 21 by the light guide fiber 26, diffused by the illumination lens 23 and radiated on a subject. Further, at the distal end portion 22, an objective lens 24 for forming an optical image of the subject with a return light from the subject and a CCD (charge-coupled device) 25 as an image pickup device disposed at the position where the optical image is formed are provided. The CCD 25 which configures image pickup means is driven (not illustrated) by a CCD drive circuit which is provided at the image processing apparatus 4 and which is not illustrated, picks up an image of the subject, converts the picked up optical image of the subject into a video signal and outputs the video signal to the image processing apparatus 4.

The light source apparatus 3 includes a light source 31 configured with a xenon lamp, or the like. The light source 31 emits a light of a wavelength band which is close to white light. On an illumination light path of the light source 31, a narrow band filter 32, a rotating filter 33 and a diaphragm 34 are disposed.

The narrow band filter 32 converts a light emitted from the light source 31 into a narrow band light and emits the light to the rotating filter 33. The rotating filter 33 limits a band of the light passing through the narrow band filter 32 to a wavelength band necessary for narrow band light observation. The diaphragm 34 adjusts a light amount by limiting a light amount of a light passing through the rotating filter 33. A diaphragm amount of the diaphragm 34 is controlled by a light adjustment control unit 49 which will be described later.

Figure 2:
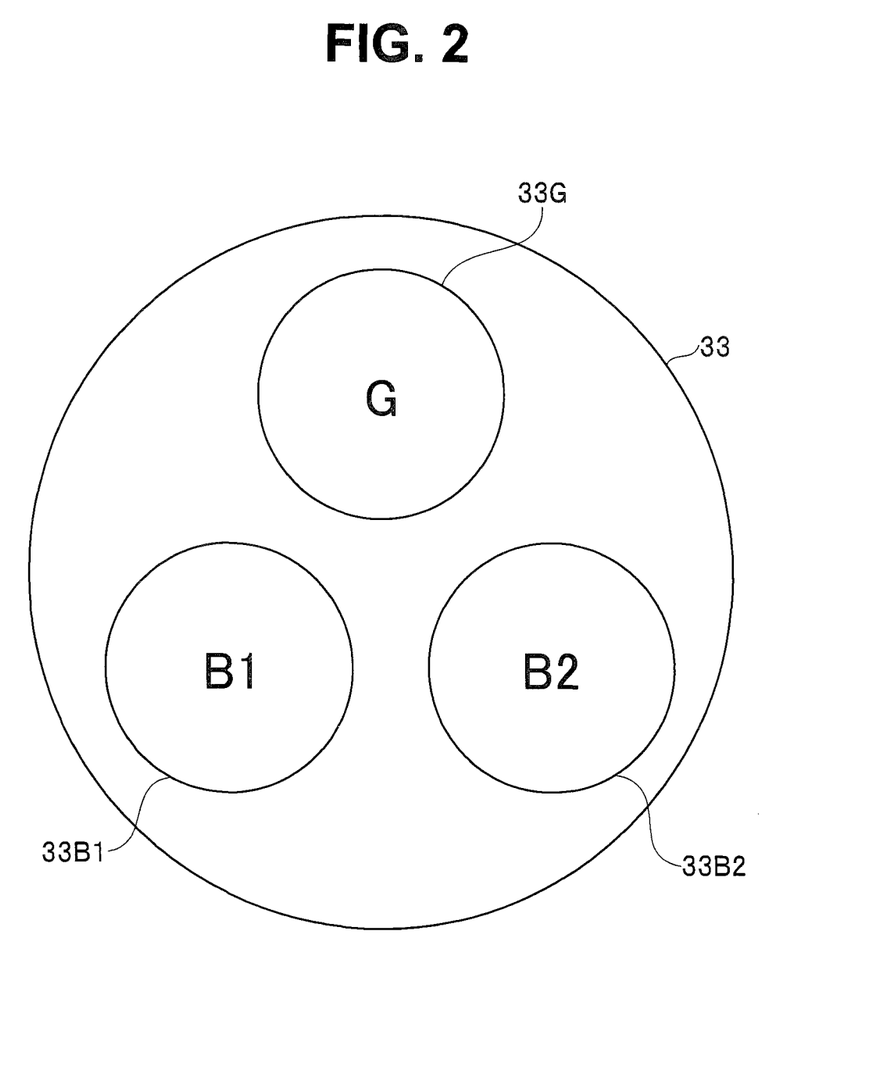
FIG. 2 is a diagram illustrating one example of a configuration of a rotating filter provided at a light source apparatus.

FIG. 2 is a diagram illustrating one example of a configuration of the rotating filter provided at the light source apparatus. The rotating filter 33 has a disc shape and includes three openings provided at equal angles in a circumferential direction, and filters 33G, 33B1 and 33B2 are respectively attached to the three openings. The filter 33G transmits a band of a green (G) wavelength band, and the filters 33B1 and 33B2 transmit a band of a blue (B) wavelength band.

With the narrow band filter 32 and the rotating filter 33, for example, a G illumination light of a narrow band of 530 to 550 nm centering around 540 nm passes through the filter 33G, for example, a B illumination light (hereinafter, referred to as a B1 illumination light) of a narrow band of 400 to 430 nm centering around 415 nm passes through the filter 33B1, and, for example, a B illumination light (hereinafter, referred to as a B2 illumination light) of a narrow band of 400 to 430 nm centering around 415 nm passes through the filter 33B2 in a similar manner to the filter 33B1. In this manner, the B1 illumination light and the B2 illumination light of a narrow band which pass through the filters 33B1 and 33B2 are lights of the same wavelength band.

The center of the rotating filter 33 is attached to a rotating shaft of a rotation motor which is not illustrated, so that the rotating filter 33 is rotationally driven. An encoder which is not illustrated is attached to the rotating shaft, or the like, of the rotation motor, and rotation of the rotation motor, that is, rotation of the rotating filter 33 can be detected by the encoder. The image processing apparatus 4 which will be described later controls rotation of the rotation motor so that a rotating speed of the rotating filter 33 becomes constant (not illustrated).

In this manner, in the present embodiment, an image of the subject is picked up using an illumination light of a narrow band from the light source apparatus 3. Therefore, compared to a case where an illumination light of a wide band which is normally widely used is used, there is a case where an amount of illumination light may not be sufficient. Particularly, because of optical transmission characteristics with the light guide fiber 26, a transmission loss tends to be greater at a short wavelength B side, and an amount of the emitted light of the B illumination light is likely to be small in a case where an illumination light is emitted from the illumination lens 23 of the distal end portion 22.

Therefore, in the present embodiment, two filters 33B1 and 33B2 having the same transmission characteristics are disposed in the circumferential direction of the rotating filter 33, the B illumination light is radiated twice on the same portion of the subject which is an observation target every time the rotating filter 33 rotates one revolution using the two filters 33B1 and 33B2, and an image is picked up twice based on the B illumination light using the return light. For example, by rotating the rotating filter 33 one revolution in a 1.5 frame period, an image is picked up twice using the B illumination light. Then, by combining the two image pickups, brightness of the picked up image (B picked up image) based on the B illumination light is improved.

Note that while an example where image pickup is performed once through illumination of the G illumination light within a 1.5 frame period and image pickup is performed twice through illumination of the B illumination light will be described, a period and the number of times for performing image pickup using a narrow band light of each color can be set appropriately.

However, because there is time lag between the B1 picked up image based on the return light of the B1 illumination light of a narrow band and the B2 picked up image based on the return light of the B2 illumination light, there is a possibility that image quality may degrade if the images are combined. Therefore, in the present embodiment, combination is not performed when a picked up image with sufficient brightness can be obtained from only one of the B1 illumination light and the B2 illumination light of a narrow band.

Further, if a picked up image with sufficient brightness cannot be obtained from only one of the B1 illumination light and the B2 illumination light of a narrow band, a picked up image based on one B illumination light is combined with a picked up image based on the other illumination light according to brightness, so that a picked up image with sufficient brightness can be obtained while suppressing image quality degradation.

In this case, in the present embodiment, the image processing apparatus 4 controls brightness according to sense of an operator by obtaining brightness of the picked up image through color conversion matrix processing.

On the other hand, according to the above-described configuration, the CCD 25 of the endoscope 2 outputs a G picked up image based on the return light of the G illumination light as a G signal, outputs a B1 picked up image based on the return light of the B1 illumination light as a B1 signal, and outputs a B2 picked up image based on the return light of the B2 illumination light as a B2 signal. That is, a video signal outputted from the endoscope 2 includes the G signal, the B1 signal and the B2 signal.

The image processing apparatus 4 has an analog processing unit 41, an A/D converter 42, a color balance processing unit 48, a digital processing unit 43, a synchronism control unit 40, a synchronism memory 40a, a composite processing unit 45, a matrix processing unit 46, a D/A converter 47, a brightness calculation processing unit 44 and a light adjustment control unit 49.

The analog processing unit 41 performs predetermined analog signal processing such as amplification processing on the video signal from the endoscope 2 and outputs the processed signal to the A/D converter 42.

The A/D converter 42 converts the output of the analog processing unit 41 into a digital video signal and outputs the digital video signal to the color balance processing unit 48.

The color balance processing unit 48 performs color balance adjustment by multiplying respective color signals (a G signal, a B1 signal and a B2 signal) included in the digital video signal outputted from the A/D converter 42 by a correction coefficient determined according to operation of a color balance adjustment switch (not illustrated) provided at a front panel of the image processing apparatus 4, and outputs the digital video signal subjected to the color balance adjustment to the digital processing unit 43.

The digital processing unit 43 performs clipping processing based on clip luminance (clip level) Yc outputted from the brightness calculation processing unit 44 on the digital video signal outputted from the color balance processing unit 48 to thereby limit an upper limit value of a luminance value of the digital video signal subjected to the clipping processing to the luminance value Yc. Further, the digital processing unit 43 separates the above-mentioned digital video signal subjected to the clipping processing into a G signal, a B1 signal and a B2 signal and outputs the G signal, the B1 signal and the B2 signal to the synchronism control unit 40 and the brightness calculation processing unit 44.

The synchronism control unit 40 stores the G signal, the B1 signal and the B2 signal outputted from the digital processing unit 43 in the synchronism memory 40a in which an R image, a G image and a B image are stored. Note that, for example, a G signal corresponding to 30 frames, a B1 signal corresponding to 30 frames and a B2 signal corresponding to 30 frames are stored in the synchronism memory 40a. The synchronism control unit 40 reads out a G signal, a B1 signal and a B2 signal for which color shift becomes minimum from the synchronism memory 40a and outputs the G signal, the B1 signal and the B2 signal to the composite processing unit 45.

Figure 3:
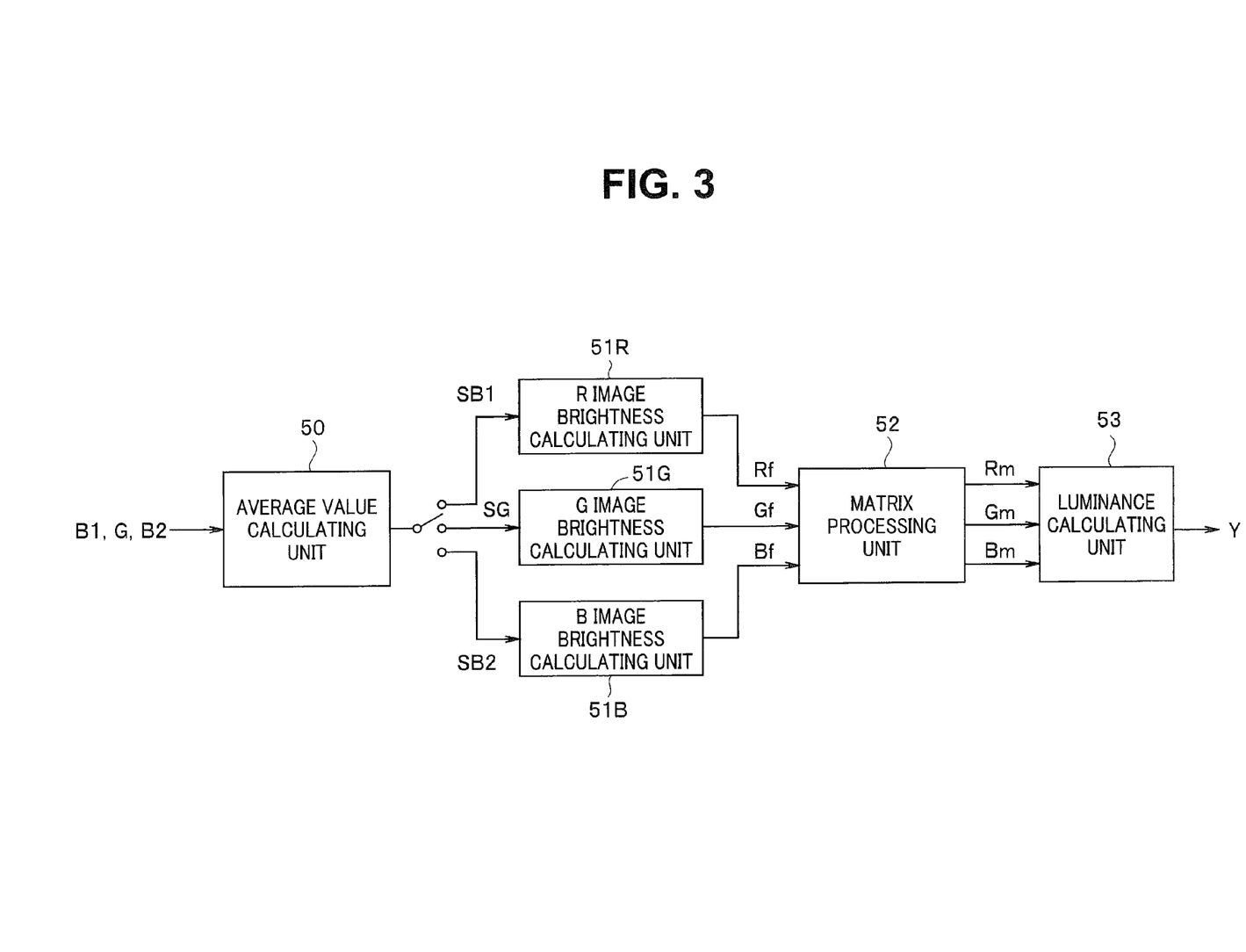
FIG. 3 is a block diagram illustrating one example of a specific configuration of a brightness calculating unit.

The brightness calculation processing unit 44 sequentially calculates brightness of a picked up image for each of 0.5 frame based on the G signal, the B1 signal and the B2 signal outputted from the digital processing unit 43. In the present embodiment, in order to evaluate brightness of the picked up image assuming a case where the picked up image is actually displayed on the monitor 5, brightness is obtained by implementing the same matrix processing as the matrix processing performed when the picked up image is displayed on the monitor 5. Further, in the present embodiment, illumination with the G illumination light and the B1 illumination light is used as master illumination which is always used for image pickup, while illumination with the G illumination light and the B2 illumination light is used as slave illumination which is accessorially used when brightness of the image is low. In order to obtain brightness of the picked up image with the master illumination, the brightness calculation processing unit 44 obtains luminance Y1 with the master illumination by utilizing the matrix processing by the matrix processing unit 52 based on the G signal and the B1 signal. Further, in order to obtain brightness of the picked up image with the slave illumination, the brightness calculation processing unit 44 obtains luminance Y2 with the slave illumination by utilizing the matrix processing by the matrix processing unit 52 based on the G signal and the B2 signal. FIG. 3 is a block diagram illustrating one example of a specific configuration of the brightness calculation processing unit.

The average value calculating unit 50 calculates an SB1 signal, an SG signal and an SB2 signal which are average values of signals corresponding to the R image, the G image and the B image.

An R image brightness calculating unit 51R, a G image brightness calculating unit 51G and a B image brightness calculating unit 51B respectively obtain brightness using the SB1 signal, the SG signal and the SB2 signal. Note that, in the present embodiment, a B1 signal is used as a signal of the R image, a G signal is used as a signal of the G image, and a B2 signal is used as a signal of the B image.

The R image brightness calculating unit 51R, the G image brightness calculating unit 51G and the B image brightness calculating unit 51B maintain the SB1 signal, the SG signal and the SB2 signal, and outputs the SB1 signal, the SG signal and the SB2 signal to the matrix processing unit 52 as Rf, Gf and Bf.

The matrix processing unit 52 performs matrix operation related to color conversion by applying Rf, Gf and Bf outputted from the R image brightness calculating unit 51R, the G image brightness calculating unit 51G and the B image brightness calculating unit 51B to the following equation (1). In this case, the matrix processing unit 52 performs matrix processing on each of the master illumination and the slave illumination through the matrix operation using the following equation (1). Note that $\alpha$, $\beta$ and $\gamma$ in the following equation (1) are matrix coefficients.

$$\begin{pmatrix} Rm \\ Gm \\ Bm \end{pmatrix} = \begin{pmatrix} 0 & \alpha & 0 \\ 0 & 0 & \beta \\ 0 & 0 & \gamma \end{pmatrix} \begin{pmatrix} Rf \\ Gf \\ Bf \end{pmatrix} \quad (1)$$

The matrix processing unit 52 supplies outputted values Rm, Gm and Bm obtained through the matrix processing on the master illumination or through the matrix processing on the slave illumination to the luminance calculating unit 53.

Note that, in the present embodiment, a G signal is supplied as the outputted value Rm, a B signal is supplied as the outputted value Gm, and a B signal is supplied as the outputted value Bm to the luminance calculating unit 53.

For example, the luminance calculating unit 53 obtains luminance Y1 with the master illumination by performing operation by applying the outputted value Rm (the G signal), the outputted value Gm (the B signal) and the outputted value Bm (the B signal) supplied from the matrix processing unit 52 to the following equation (2).

$$Y1 = 0.3Rm + 0.59Gm + 0.11Bm \qquad (2)$$
$$= 0.3(\alpha \cdot SG) + 0.59(\beta \cdot SB1) + 0.11(\gamma \cdot SB1)$$

Further, for example, the luminance calculating unit 53 obtains luminance Y2 with the slave illumination by performing operation by applying the outputted value Rm (the G signal), the outputted value Gm (the B signal) and the outputted value Bm (the B signal) supplied from the matrix processing unit 52 to the following equation (3).

$$Y2 = 0.3Rm + 0.59Gm + 0.11Bm \qquad (3)$$
$$= 0.3(\alpha \cdot SG) + 0.59(\beta \cdot SB2) + 0.11(\gamma \cdot SB2)$$

The brightness calculation processing unit 44 obtains a difference (Ys−Y1)=ΔY1 which is a difference between target luminance (brightness target value) Ys and luminance Y1. When ΔY1≤0, that is, when target brightness can be obtained only with the master illumination, the brightness calculation processing unit 44 sets a value of a composite ratio a (0≤a≤1) of the picked up image with the slave illumination at 0 and respectively sets values of clip luminance Yc and target luminance Ys at predetermined values. On the other hand, when ΔY1>0, that is, when target brightness cannot be obtained only with the master illumination, the brightness calculation processing unit 44 obtains a value of the composite ratio a through operation using the following equation (4) and respectively sets the clip luminance Yc and the target luminance Ys according to the obtained value of the composite ratio a.

$$\Delta Y1 = Y2 \times a \quad a = \Delta Y1/Y2 \qquad (4)$$

In the narrow band light observation, picked up images based on return lights of the G illumination light and the B illumination light of a narrow band are used. The matrix processing unit 46 which will be described later, generates a signal component of an RGB image from the G picked up image and the B picked up image obtained through image pickup using the narrow band light, through the matrix processing (color conversion matrix processing).

The matrix processing at the matrix processing unit 52 of the brightness calculation processing unit 44 is the same processing as the matrix processing at the matrix processing unit 46. That is, the matrix operation by the brightness calculation processing unit 44 is performed to obtain a signal corresponding to an RGB input of the monitor 5, and luminance obtained by the brightness calculation processing unit 44 corresponds to luminance of the image displayed on the monitor and corresponds to brightness of the image sensed by the operator when the operator observes the monitor 5.

Note that it is obvious that the coefficients in the above-described equations (2) and (3) used in the operation by the luminance calculating unit 53 can be varied according to color tone desired as a narrow band light observation image to be displayed on the monitor 5.

The brightness calculation processing unit 44 outputs the composite ratio a obtained through the operation of the above-described equation (4) to the composite processing unit 45 and outputs clip luminance Yc set according to the value of the composite ratio a to the digital processing unit 43. Further, the brightness calculation processing unit 44 outputs the target luminance Ys set according to the value of the composite ratio a, and a difference value ΔY1 to the light adjustment control unit 49.

The light adjustment control unit 49 generates a light adjustment signal for adjusting a diaphragm amount of the diaphragm 34 based on the target luminance Ys and the difference value ΔY1 outputted from the brightness calculation processing unit 44 and outputs the light adjustment signal. More specifically, the light adjustment control unit 49 generates a light adjustment signal for adjusting the diaphragm amount of the diaphragm 34, for example, so as to be close to the target luminance Ys outputted from the brightness calculation processing unit 44, that is, so that the value of the difference value ΔY1 outputted from the brightness calculation processing unit 44 is close to 0 and outputs the light adjustment signal. With such control by the light adjustment control unit 49, the light amount of the G illumination light and the light amount of the B illumination light (the B1 illumination light and the B2 illumination light) are adjusted.

The composite processing unit 45 combines the image picked up with the master illumination and the image picked up with the slave illumination based on the composite ratio a. That is, when the composite ratio a is 0, the composite processing unit 45 outputs the image picked up with the master illumination from the digital processing unit 43, that is, a signal obtained only using the G signal and the B1 signal to the matrix processing unit 46. Further, when the composite ratio a is not 0, the composite processing unit 45 combines the image picked up with the slave illumination, that is, a signal obtained from the G signal, the B2 signal and the composite ratio a with the signal based on the image picked up with the master illumination.

Further, for example, when brightness of the G illumination light is extremely higher than brightness of the B illumination light, that is, when the value of the composite ratio a becomes 1, there is no electrically excessive multiplication, so that it is possible to suppress increase of noise.

The following equation (5) is an arithmetic equation used when the image picked up with the master illumination and the image picked up with the slave illumination are combined based on the composite ratio a.

Note that Rin, Gin and Bin in the following equation (5) indicate inputs of the R image, the G image and the B image. More specifically, in the narrow band light observation in the present embodiment, the B2 signal from the synchronism control unit 40 is inputted to the composite processing unit 45 as Rin in the following equation (5), the G signal from the synchronism control unit 40 is inputted to the composite processing unit 45 as Gin in the following equation (5), and the B1 signal from the synchronism control unit 40 is inputted to the composite processing unit 45 as Bin in the following equation (5). Further, Rt, Gt and Bt in the following equation (5) indicate outputs of the R image, the G image and the B image of the composite signal. Note that while Rt=B2 in the following equation (5), the output of the R image supplied to the monitor 5 becomes substantially 0 through matrix processing which will be described later.

$$\begin{pmatrix} Rt \\ Gt \\ Bt \end{pmatrix} = \begin{pmatrix} 1 & 0 & 0 \\ 0 & 1+a & 0 \\ a & 0 & 1 \end{pmatrix} \begin{pmatrix} Rin \\ Gin \\ Bin \end{pmatrix} = \begin{pmatrix} 1 & 0 & 0 \\ 0 & 1+a & 0 \\ a & 0 & 1 \end{pmatrix} \begin{pmatrix} B2 \\ G \\ B1 \end{pmatrix} = \begin{pmatrix} B2 \\ (1+a)G \\ a \cdot B2 + B1 \end{pmatrix} \quad (5)$$

The composite processing unit 45 obtains a composite signal by performing operation using the above-described equation (5) and outputs the obtained composite signal to the matrix processing unit 46.

The matrix processing unit 46 obtains a signal corresponding to an RGB input of the monitor 5 through matrix processing. The following equation (6) indicates an example of the matrix processing by the matrix processing unit 46. Note that $\alpha$, $\beta$ and $\gamma$ in the following equation (6) are matrix coefficients and set so as to be the same values as $\alpha$, $\beta$ and $\gamma$ in the above-described equation (1). Further, Rout, Gout and Bout in the following equation (6) indicate outputs of the R image, the G image and the B image after the matrix processing.

$\alpha$, $\beta$ and $\gamma$ can be changed according to color tone desired for narrow band light observation. $\alpha$, $\beta$ and $\gamma$ are obtained so as to fall within a range of, for example, 0.7 and 1.5 so that $\alpha$, $\beta$ and $\gamma$ is not too great or not too small, and selected from a plurality of candidates. If $\alpha$, $\beta$ and $\gamma$ exceed the range, noise may increase or saturation may be likely to occur. Under the conditions, only $\alpha$ is determined to fall within a range of 0.35 and 0.75 taking into account (1+a) in the above-described equation (5). Of course, because (1+a) in the equation (5) is taken into account, noise may not increase or saturation may not increase. However, it is necessary to expand a bit width so that a dynamic range is not missed.

$$\begin{pmatrix} Rout \\ Gout \\ Bout \end{pmatrix} = \begin{pmatrix} 0 & \alpha & 0 \\ 0 & 0 & \beta \\ 0 & 0 & \gamma \end{pmatrix} \begin{pmatrix} Rt \\ Gt \\ Bt \end{pmatrix} \quad (6)$$

In the above-described equation (6), Rt is multiplied by 0. Therefore, while Rt=B2 in the above-described equation (5), Rt may be Rt=0.

The D/A converter 47 converts the output of the matrix processing unit 46 into an analog signal and outputs the analog signal to the monitor 5. That is, Rout, Gout and Bout in the equation (6) are provided to the monitor 5 as RGB inputs. The monitor 5 displays the narrow band light observation image according to the inputted RGB inputs.

Next, operation of the endoscope apparatus 1 having the above-described configuration will be described.

The operator connects the connector 27 of the endoscope 2 to the light source apparatus 3 and the image processing apparatus 4 as illustrated in FIG. 1 when the operator uses the endoscope apparatus 1. By this means, a connection state illustrated in FIG. 1 can be obtained. The operator puts the light source apparatus 3, the image processing apparatus 4 and the monitor 5 into an operation state by operating a power supply switch which is not illustrated and performs operation for narrow band light observation.

A light radiated from the light source 31 is converted into a G illumination light, a B1 illumination light and a B2 illumination light of a narrow band by the narrow band filter 32 and the rotating filter 33, and supplied to the endoscope 2 after brightness is adjusted by the diaphragm 34. Each illumination light is sequentially and substantially continuously radiated, for example, in a cycle of 1/20 seconds from the illumination lens 23 toward the subject side via the light guide fiber 26.

At timings at which the G illumination light, the B1 illumination light and the B2 illumination light are respectively radiated on the same portion of the subject, the CCD 25 picks up an optical image using return lights from the portion. Through photoelectric conversion of the CCD 25, a G signal, a B1 signal and a B2 signal respectively corresponding to the return lights of the G illumination light, the B1 illumination light and the B2 illumination light are obtained. The video signal including the G signal, the B1 signal and the B2 signal is provided to the image processing apparatus 4 from the endoscope 2.

Note that the B1 signal and the B2 signal which are signals obtained by picking up the image with the same exposure amount using the illumination light of the same wavelength band, can be obtained under substantially the same conditions except that there is a small timing difference within one frame.

The video signal inputted to the image processing apparatus 4 is converted into a digital signal by the A/D converter 42 after the video signal is subjected to predetermined analog processing by the analog processing unit 41. The digital video signal from the A/D converter 42 is inputted to the digital processing unit 43 after the digital video signal is subjected to color balance adjustment by the color balance processing unit 48.

The digital processing unit 43 performs clipping processing based on clip luminance Yc outputted from the brightness calculation processing unit 44 on the digital video signal outputted from the color balance processing unit 48, separates the digital video signal subjected to the clipping processing into a G signal, a B1 signal and a B2 signal and outputs the G signal, the B1 signal and the B2 signal to the synchronism control unit 40 and the brightness calculation processing unit 44.

The brightness calculation processing unit 44 respectively calculates luminance Y1 with master illumination and luminance Y2 with slave illumination through the matrix processing at the matrix processing unit 52. Further, the brightness calculation processing unit 44 calculates a difference value $\Delta Y1$ between the target luminance Ys and the luminance Y1, obtains a composite ratio a using the calculated difference value $\Delta Y1$, and, further, sets values of the clip luminance Yc and the target luminance Ys according to the obtained value of the composite ratio a.

Here, according to the present embodiment, the target luminance Ys is set at a predetermined initial value Ydb at a timing immediately after the image processing apparatus 4 is activated, and is set at a value according to the value of the composite ratio a when the image processing apparatus 4 is put into an operation state. More specifically, for example, the target luminance Ys is set at luminance Yt when the composite ratio a is equal to or greater than 0 and less than a predetermined threshold TH1 and is set at luminance Yu which is greater than the luminance Yt when the composite ratio a is equal to or greater than the predetermined threshold TH1 and equal to or less than 1.

Note that according to the present embodiment, in addition to a case where the target luminance Ys is set according only to the value of the composite ratio a, when, for example, it is detected that the color balance adjustment by the color balance processing unit 48 is performed using a correction coefficient (of less than 1.0) which reduces a signal level of each color signal included in the digital video signal outputted from the A/D converter 42, the brightness calculation processing unit 44 may set the target luminance Ys at luminance Yw which is equal to or greater than the luminance Yu regardless of the value of the composite ratio a.

Figure 4:
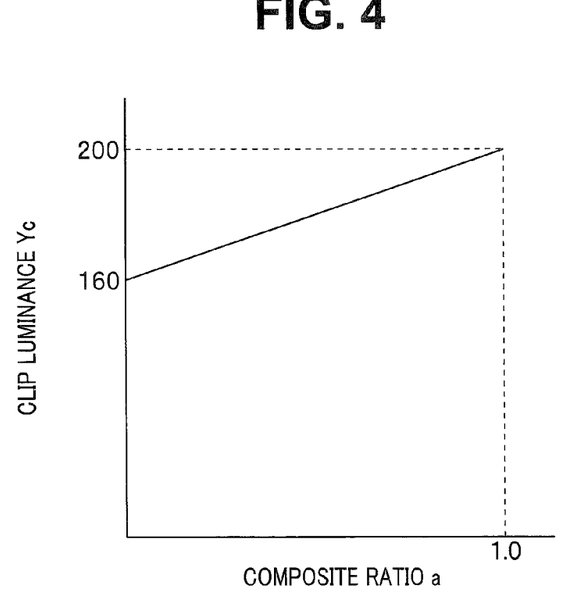
FIG. 4 is a diagram illustrating one example of correlation between a composite ratio a and clip luminance Yc.

On the other hand, according to the present embodiment, the clip luminance Yc is set at a predetermined initial value Ydc (for example, Ydc=200) at a timing immediately after the image processing apparatus 4 is activated, and is set at a value according to the value of the composite ratio a when the image processing apparatus 4 is put into an operation state. More specifically, the clip luminance Yc is, for example, set based on data in which correlation between the composite ratio a and the clip luminance Yc is specified as illustrated in FIG. 4. FIG. 4 is a diagram illustrating one example of correlation between the composite ratio a and the clip luminance Yc.

According to FIG. 4, when a=0, the clip luminance Yc is set as Yc=160, when a=1, the clip luminance Yc is set as Yc=200, and when 0<a<1, the clip luminance Yc is set so as to increase within a range of 160<Yc<200 in proportion to increase of the value of a. That is, according to FIG. 4, within a range of 0≤a≤1 and 160≤Yc≤200, the composite ratio a is in proportion to the clip luminance Yc.

Figure 5:
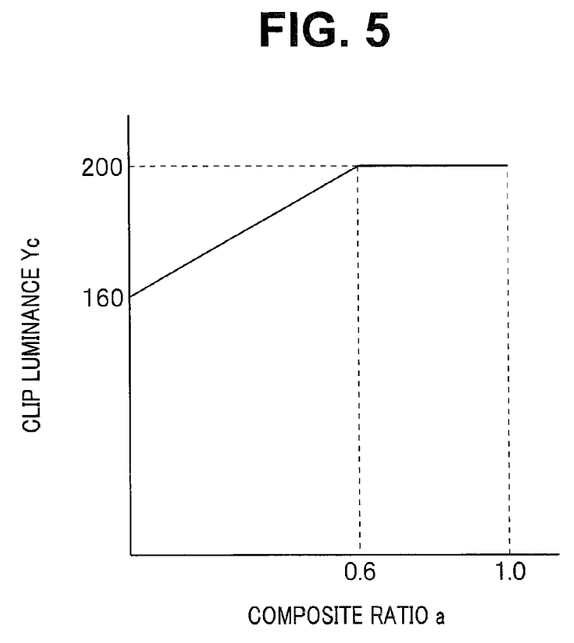
FIG. 5 is a diagram illustrating an example different from the example of FIG. 4, of correlation between the composite ratio a and the clip luminance Yc.

Note that according to the present embodiment, the clip luminance Yc may be set based on data in which correlation between the composite ratio a and the clip luminance Yc is specified as illustrated in FIG. 5. FIG. 5 is a diagram illustrating a different example from the example of FIG. 4, of the correlation between the composite ratio a and the clip luminance Yc.

According to FIG. 5, when a=0, the clip luminance Yc is set as Yc=160, when 0.6≤a≤1, the clip luminance Yc is set as Yc=200, and, when 0<a<0.6, the clip luminance Yc is set so as to increase within a range of 160<Yc<200 in proportion to increase of the value of a. That is, according to FIG. 5, in a range of 0≤a≤0.6 and 160≤Yc≤200, the composite ratio a is in proportion to the clip luminance Yc.

The brightness calculation processing unit 44 outputs the composite ratio a obtained as described above to the composite processing unit 45 and outputs the clip luminance Yc set as described above to the digital processing unit 43. Further, the brightness calculation processing unit 44 outputs the target luminance Ys set as described above, and the difference value ΔY1 to the light adjustment control unit 49.

The light adjustment control unit 49 generates and outputs a light adjustment signal for adjusting a diaphragm amount of the diaphragm 34 based on the target luminance Ys and ΔY1 outputted from the brightness calculation processing unit 44.

The composite processing unit 45 obtains a composite signal by applying the composite ratio a outputted from the brightness calculation processing unit 44 to the above-described equation (5), and outputs the obtained composite signal to the matrix processing unit 46.

The composite signal outputted from the composite processing unit 45 is provided to the matrix processing unit 46 where the composite signal is subjected to matrix processing, and signals of an R image, a G image and a B image in a display system can be obtained. The output of the matrix processing unit 46 is returned to an analog signal by the D/A converter 47 and supplied to the monitor 5.

As described above, according to the present embodiment, it is possible to set the target luminance Ys and the clip luminance Yc according to the value of the composite ratio a. Therefore, according to the present embodiment, for example, even if a pixel size of the CCD 25 is small (a saturation level is low), it is possible to suppress degradation of image quality caused due to variation of the saturation level for each pixel, so that it is possible to improve image quality of a narrow band light observation image compared to the conventional techniques.

Note that, according to the present embodiment, for example, by providing a frame memory (not illustrated) which is capable of accumulating composite signals outputted from the composite processing unit 45 corresponding to a plurality of frames at the image processing apparatus 4, when the monitor 5 is instructed to display a freeze image, a composite signal having a minimum value of the composite ratio a may be selected from the respective composite signals accumulated in the memory and may be outputted to the matrix processing unit 46.

Further, according to the present embodiment, for example, by providing a frame memory (not illustrated) which is capable of accumulating composite signals outputted from the composite processing unit 45 corresponding to a plurality of frames at the image processing apparatus 4, when the monitor 5 is instructed to display a freeze image, a composite signal for which a predetermined time period or less has elapsed from a timing of the instruction and for which the value of the composite ratio a is equal to or less than a predetermined value may be selected from the composite signals accumulated in the memory and may be outputted to the matrix processing unit 46.

Further, according to the present embodiment, for example, when peripheral equipment such as an image filing apparatus is connected to the image processing apparatus 4, setting of the peripheral equipment and setting of the image processing apparatus 4 may be switched in association with each other.

Further, according to the present embodiment, for example, information indicating positional relationship between a central position of the objective lens 24 and a central position of an effective pixel region of the CCD 25 may be stored in advance in a memory (not illustrated) provided at the endoscope 2, and position adjustment processing for adjusting the positions so that the central position of an observation image to be displayed on the monitor 5 is aligned with the central position of the objective lens 24, may be performed based on the information read from the memory.

Further, according to the present embodiment, for example, when color balance adjustment by the color balance processing unit 48 is performed using a correction coefficient (of less than 1.0) which reduces a signal level of each color signal included in the digital video signal outputted from the A/D converter 42, control may be performed so as to reduce a light amount of the light source 31.

Further, according to the present embodiment, for example, a plurality of scope switches (not illustrated) which are capable of issuing various instructions according to operation of an operator may be provided at the endoscope 2, and an instruction which can be implemented may be assigned as appropriate through operation of the plurality of scope switches according to a result indicating a detected function which can be used in the endoscope 2 connected to the image processing apparatus 4.

Further, according to the present embodiment, for example, it is also possible to reduce color shift of a freeze image to be displayed on the monitor 5 by making a rotation speed of the rotating filter 33 in the case where an image of an object which moves violently is picked up faster than a rotation speed of the rotating filter 33 in the case where an image of an object which moves gently is picked up.

Further, according to the present embodiment, for example, when a light source apparatus provided with an LED which emits a G illumination light, an LED which emits a B1 illumination light, and an LED which emits a B2 illumination light, is used, a light emission time period for enabling generation of a narrow band light observation image having brightness appropriate for observation may be set for each LED, and a frame rate at which a narrow band light observation image is displayed on the monitor 5 may be changed according to the set light emission time period for each LED.

Further, according to the present embodiment, for example, by increasing or decreasing a drive current (lamp current) of the light source 31, the light amount of the light radiated from the light source apparatus 3 may be adjusted to a light amount of a range beyond the range which can be adjusted with a diaphragm amount of the diaphragm 34.

Further, the light adjustment control unit 49 of the present embodiment may be configured to generate a light adjustment signal based on the target luminance Ys and ΔY1 outputted from the brightness calculation processing unit 44 and a detection result of a light distribution state of the illumination light radiated from the light guide fiber 26.

Of course, the present invention is not limited to the above-described embodiment, and various change and application can be made within the scope not departing from the gist of the present invention.

What is claimed is:

1. An endoscope apparatus comprising:
   a light source configured to emit an illumination light of a first band once and emit an illumination light of a second band N times (where N is an integer of N≥2), within a predetermined time period;
   an image pickup sensor configured to pick up an image of a subject illuminated by each of the illumination lights emitted from the light source within the predetermined time period and to output an image pickup signal; and
   a processor comprising hardware, wherein the processor is configured to:
   clip an upper limit value of a luminance value in the image pickup signal according to a clip level, the processor further configured to separate the image pickup signal subjected to the clipping processing into a first image pickup signal obtained by picking up an image of the subject illuminated by the illumination light of the first band emitted once within the predetermined time period, a second image pickup signal obtained by picking up an image of the subject illuminated by the illumination light of the second band emitted K times (wherein K is an integer of 1≤K<N) within the predetermined time period, and a third image pickup signal obtained by picking up an image of the subject illuminated by the illumination light of the second band emitted (N-K) times within the predetermined time period, and to output the separated first, second and third image pickup signals;
   calculate a first luminance based on the first and second image pickup signals outputted from the clipping step and calculate a second luminance based on the first and third image pickup signals outputted from the clipping step;
   combine a first image generated by the first and second image pickup signals with a second image generated by the first and third image pickup signals; and
   calculate a composite ratio of the second image to be combined with the first image based on a difference value between a target luminance and the first luminance, and to set the clip level according to the calculated composite ratio.

2. The endoscope apparatus according to claim 1, wherein the processor is further configured to calculate, as the composite ratio, a value obtained by dividing the difference value by the second luminance value.

3. The endoscope apparatus according to claim 2, wherein the processor is further configured to calculate the first luminance based on a processing result of performing a predetermined color conversion processing on the outputted first and second image pickup signals, and to calculate the second luminance based on a processing result of performing the predetermined color conversion processing on the outputted first and third image pickup signals.

4. The endoscope apparatus according to claim 1, wherein the processor is further configured to adjust a light amount of the illumination light of the first band and a light amount of the illumination light of the second band by performing control on the light source based on the target luminance and the difference value, wherein
   the processor is further configured to set the target luminance according to the composite ratio.

5. The endoscope apparatus according to claim 1, wherein the processor is further configured to increase the clip level within a predetermined range in proportion to increase of the composite ratio.

6. The endoscope apparatus according to claim 4, wherein, when the composite ratio is equal to or greater than 0 and less than a predetermined threshold, the processor sets the target luminance at a first value, and, when the composite ratio is equal to or greater than the predetermined threshold and equal to or less than 1, the processor sets the target luminance at a second value which is greater than the first value.

7. The endoscope apparatus according to claim 6, wherein the processor is further configured to perform color balance adjustment on the first image pickup signal and the second image pickup signal before the clipping step,
   wherein when it is detected that color balance adjustment to increase a signal level of the image pickup signal outputted from the image pickup sensor is performed by the processor, the processor sets the target luminance at a third value which is equal to or greater than the second value regardless of the composite ratio.

8. The endoscope apparatus according to claim 1, wherein N=2 and K=1.

* * * * *